United States Patent [19]
Oomichi et al.

[11] Patent Number: 5,193,405
[45] Date of Patent: Mar. 16, 1993

[54] UNDERWATER MOBILE TYPE INSPECTION SYSTEM

[75] Inventors: Takeo Oomichi; Yukio Hukagawa, both of Takasago; Kazuto Sawaragi, Kobe; Kyoichi Aizawa, Kobe; Kiyoshi Tachibana, Kobe; Junji Nakayama, Kobe; Tomio Aoyama, Kobe; Kyoichi Yoshioka, Kobe; Mitsushi Ideo, Kobe, all of Japan

[73] Assignee: Mitsubishi Jukogyo Kabushiki Kaisha, Tokyo, Japan

[21] Appl. No.: 709,300

[22] Filed: May 31, 1991

[30] Foreign Application Priority Data

Jun. 5, 1990 [JP] Japan ............................. 2-58755[U]

[51] Int. Cl.⁵ .......................................... G01M 19/00
[52] U.S. Cl. .................................................. 73/865.8
[58] Field of Search .................... 73/865.8, 866.5, 623; 376/245, 249, 252; 358/99, 106

[56] References Cited

U.S. PATENT DOCUMENTS 3,780,571 12/1973 Wiesener ............................. 376/249
4,345,658 8/1982 Danel et al. ........................ 376/249
4,502,407 3/1985 Stevens .................................. 358/99
4,964,059 10/1990 Sugaya et al. ......................... 73/623

FOREIGN PATENT DOCUMENTS 2636038 3/1990 France .
0129255 8/1983 Japan .................................... 73/623

Primary Examiner—Robert Raevis
Attorney, Agent, or Firm—McAulay Fisher Nissen Goldberg & Kiel

[57] ABSTRACT

A underwater mobile type inspection system is disclosed wherein said system comprises a multi-articulated manipulator with a probe attached at its tip end thereof. A pivot base supports the proximal end of the manipulator for free rotation and is provided with a propulsion device. An anchoring base is attached to the bottom of said pivot base via a pivot driving mechanism. An adhesion device and a mobile vehicle device are provided, both of which are mounted on the outer periphery of said anchoring base. The inspection system may be applicable to a defect finding operation, other inspecting procedures, cleaning and recovery operations of foreign materials in large-sized vessels, such as nuclear reactor pressure vessels, water pools and storage tanks etc.

17 Claims, 19 Drawing Sheets

○ CENTER OF GRAVITY
⊗ CENTER OF BUOYANCY
UNDERWATER WEIGHT = 0 kgf

MOTION OF MOBILE DEVICE
FIG. 12(a) IF NUMBERS OF ROTATION ARE THE SAME, IT MOVES STRAIGHT
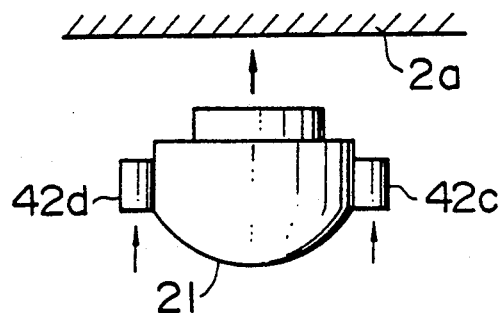
FIG. 12(b) IF NUMBERS OF ROTATION DIFFER, IT TURNS TO LEFT
(IF 42d > 42c, IT TURNS RIGHT)
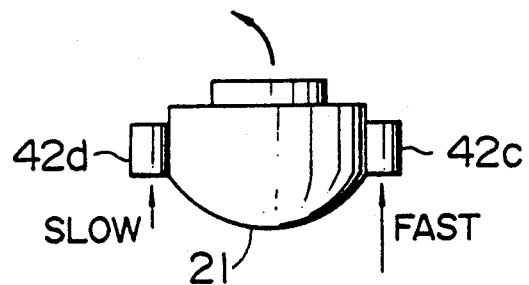
FIG. 12(c) IF DIRECTIONS OF ROTATION ARE DIFFERENT, IT ROTATES ON THE SPOT ( |42c| = |42d| )
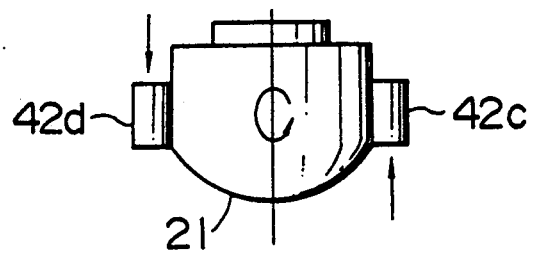

UNDERWATER MOBILE TYPE INSPECTION SYSTEM

BACKGROUND OF THE INVENTION

1. Field of the Invention

The present invention relates to an underwater mobile type inspection system for use in various operations, such as the ultrasonic inspection of a nuclear reactor pressure vessel in nuclear power stations, the cleaning of large containers and the recovery of foreign objects from the water.

2. Description of the Related Art

Conventionally, an ultrasonic inspection apparatus as one shown, for example, in FIG. 18 has been used as one type of inspection system for detecting defects in internal walls of large containers.

Referring to FIG. 18, an ultrasonic inspection apparatus will be described hereinbelow by way of an example which may be used to detect defects in the welded portion of the nuclear reactor pressure vessel.

In FIG. 18, the ultrasonic inspection apparatus 1 comprises a ring-like rail 4 which is attached to the outer end of the rotatable legs 6 which in turn extend radially and outwardly from the body portion thereof. The ultrasonic inspection apparatus 1 is fixed in position to an upper flange 3 of a nuclear reactor pressure vessel 2 via support legs 5 which extend from the rail 4 and a guide stud 11 when a head closure (not shown) is removed. Suspending from the body portion of the inspection apparatus 1 downwardly is a supporting column 7 along which a manipulator 10 having a probe assembly 9 may be movable by means of a driving device 8. In such a prior ultrasonic inspection apparatus 1, the positioning operation of the manipulator 10 is performed by the rotary movement of the rail 4 and the vertical movement of the driving device 8, thereby accomplishing ultrasonic inspection of any welded regions in the nuclear reactor pressure vessel 2.

FIG. 19 shows a typical example of prior art pool cleaning apparatus which is adapted to move and perform a desired operation in the water as needed.

In FIG. 19, there is shown a pool cleaning apparatus 200. The pool cleaning apparatus 200 is first transported to a pool side area, and then submerged into the pool water until it sinks to the bottom of the pool by gravity. Then, the cleaning apparatus 200 is actuated to suck and remove foreign objects or the like from the pool water by means of a pump 202, while it travels on wheels 201.

A similar cleaning operation as described above is undertaken along and on the wall surface of the pool.

FIG. 20 shows a tank cleaning apparatus which may be used to clean the inner wall surface of a container, such as a tank.

The tank cleaning apparatus 300 operates to clean the internal surface of the tank by means of a rubbing brush 302 which is attached at the top end of the apparatus body 300, while it is driven by means of screws 301 to move floating on the water surface.

Another example of an apparatus designed for flaw detection is an apparatus which is provided with a submerging device (such as one shown, for example, in the Japanese Patent Applications No.SHO 58-246435 and No.SHO 59-35508 etc.). This type of flaw detection apparatus is designed such that it comprises a submerging device body adapted to be driven to travel under the water by a propulsion unit, and the submerged device body is provided with a slewing mechanism, of two degrees of freedom as the case may be, having a probe.

However, such apparatuses as shown in FIG. 18, FIG. 19, and FIG. 20 have problems as described below.

First, the apparatus of the construction as shown in FIG. 18 needs a rail 4 which is bulky and heavy in weight for attachment on the body 2 of the large container, and other ancillary equipments, such as support legs 5, in order to guide a probe to a location where a flaw detecting operation should be undertaken. Consequently, not only does the apparatus need plenty of time and manual labors to assemble and attach and adjust these components, but also reduction of the exposure rate of operators to radiation and speed up of its operation cannot be accomplished when the apparatus is applied to detect flaws in the nuclear reactor pressure vessel. Thus, a straight forward, compact and lightweight apparatus has been desired.

Additionally, when the apparatus having the construction as shown in FIG. 19 is intended to be used in a tank provided with a nozzle or the like, the travelling range of the apparatus is restricted, and the apparatus may not perform an intended operation directed to the internal surface of the nozzle (for example, cleaning or flaw detection operation). Besides, since the means for moving the apparatus along the wall surface is the wheels 201, it is impossible for the apparatus to run over the corner portion of the tank. Thus, if the apparatus must be operated in separate and greatly spaced locations (for example, if the apparatus must be shifted in 180° opposite directions along the vertical wall surface), it is necessary to lift and then shift the apparatus body 200 and guide it again to a location where an operation is to be performed, and thus plenty of time is needed.

Moreover, as to the construction as shown in FIG. 20, it is necessary to run the water out of the tank so as to lower the level, since the apparatus moves floating on the water surface, although the apparatus can quickly move in a plane. Such run of water out of the tank is time-consuming.

Additionally, when the apparatuses as shown in FIG. 19 and FIG. 20 are applied to flaw detection operation, some degree of a thrust force (normally in the magnitude of several kgf) is needed to press the probe against a subject to be proved. Furthermore, since an elevated precision in maintaining a locus of probe motion and a constant speed of traverse motion are required, the essential requirements described above may not be derived from the utilization of driving means, such as wheels 201 and propulsion screw 301, and thus the prior apparatus may not be usable in flaw detecting operation. Furthermore, since even the flaw detection device having a submerging device does not allow its submerging device body to come into contact with the internal wall surface of the large container, and the submerging device body is constantly floating in the water, its positioning control has been difficult.

As described above, there has been no apparatus provided so far which can carry out a flaw detection operation in a container with a higher work efficiency.

SUMMARY OF THE INVENTION

The present invention has been made in consideration of the above-mentioned backgrounds, and a principal object of the invention is to provide an inspection apparatus which is movable freely along the internal surface of a large container, without bulky and heavy ancillary equipments to be attached to the container, while ensuring a flaw detection operation with an enhanced precision.

The underwater mobile type inspection system according to the present invention is constituted with one or all of the components as described below.

A1. The system comprises a running gear which can actuate the system to move along the internal wall surface of a large container full of water, an anchoring carriage including an adhesion device for securing the carriage by an adhesion force to the wall surface, a slewing base which is freely and pivotably attached to the anchoring carriage body via a turning mechanism, said base having a propulsion unit for propelling the apparatus in two or more directions, and an orientation marker including two or more axes which are fitted to the base.

A2. The system's self-weight is designed to be 0 kgf in the water, and it comprises a propulsion unit which can actuate the system to travel in the water in two or more directions in a three-dimensional space, a running gear which drives the system to move along the internal wall surface of the large container, an adhesion device for securing the system body to the wall surface by an adhesion force, and a turning base including an orientation marker having two or more axes.

A3. To allow for various kinds of flaw detection operations, the system is provided with a manipulator having six or more axes.

A4. To orient the position of the system, the system is provided with a distance determining device at a location spaced from the system body, the distance determining device having a driving unit with two or more axes.

B1. The distance determining device is provided with a corner cube as an orientation marker, and a global light source is positioned at the central position of the corner cube for use to determine the position of the marker.

B2. The number of the propulsion units to be arranged is six in total, i.e., two units for submerging and floating the system and four units for moving the system toward and away from the wall surface.

B3. To use the cable of smaller diameter thereby reducing its weight, a driver for a driving motor, an E/O or O/E converter etc. are provided inside the turning base.

B4. To ensure for the system a free movement along the wall surface, an independent four-wheels suspension and an independent steering mechanism are provided. A meter for calculating the number of rotation of the wheel is provided to determine a distance which has been travelled by the system.

B5. Four adhesion pads are arranged vertically and horizontally to be symmetrical with the right and left adhesion pads arranged to be located adjacent to the flaw detecting position (relative to the upward and the downward directions of the anchoring carriage) of the manipulator.

C1. To establish a positional stability in the water, the system is designed such that its center of buoyancy may be located vertically above its center of gravity with regard to a positional relationship between the center of gravity and the center of buoyancy.

D1. A laser beam is used as a non-contact type distance determining means, which allows an operator to determine a distance based upon a phase difference between a signal emitted and a signal reflected back off the corner cube.

D2. The distance determining device is mounted upon a guide stud which may be used as a reference point for calculation of an absolute position of the system body.

E1. The elbow axis and the shoulder axis of the manipulator are connected together through a linkage, and a counterweight is arranged at the distal end of the linkage.

In accordance with the teachings of the present invention, the underwater mobile type inspection system will be described hereinbelow with its application for flaw detection of a nuclear reactor pressure vessel (large container).

The mobile device comprises a propulsion unit and a running gear, and has a weight of 0 kgf in the water, wherein it is designed such that its center of gravity may be positioned below the center of buoyancy in the vertical direction. Consequently, the system may move to any desired position within the nuclear reactor pressure vessel and also travel along the inner wall surface of the vessel.

When the system is guided to a location where a flaw detecting operation is carried out under the driving action as above-mentioned, the system is secured in position on an inner wall surface of the vessel by means of adhesion means attached to the mobile device, and the flaw detecting operation can be carried out by means of a manipulator. Since the adhesion pads are arranged so that they may occupy a space of maximum span to counter a moment which is caused by the flaw detecting operation of the manipulator, a stable operation for flaw detection may be accomplished in the system. Furthermore, a counterweight is provided for further improvement of the operational precision of the system. As a result, the manipulator can retain its center of gravity on the axis of the shoulder, even when the position of the manipulator is varied, and thus no variation in the magnitude of moment occurs, thereby preventing the system body from making any rattling movement (i.e., the axis of the shoulder of the manipulator does not move during a flaw detecting operation).

Besides, it is possible to move the manipulator upwardly relative to the nuclear reactor vessel by the slewing mechanism of the turning base and thus the flaw detecting operation not only for the nozzle, but also for the flange ligament portion, may be carried out from the internal surface of the vessel. Consequently, flaw detection covering any location to be inspected may be completely accomplished by the system of the present invention. The absolute position of the mobile device can be determined by means of the orientation marker and the distance determining device arranged on the guide stud, using the guide stud as a reference point.

The underwater mobile type inspection system in accordance with the present invention can move to any desired position within the large vessel, allowing its compact assembly with a reduced weight as well as an easy assembly, installation and adjustment.

Furthermore, the underwater inspection system of the present invention can be moved in a short period of time driven by the propulsion unit in all directions in a three-dimensional space faster than the conventional apparatus for similar purposes in the underwater operation, even when a desired position of operation is substantially remote away. Moreover, the absolute position of the mobile device can be determined, and consequently a highly precise flaw detection operation may be carried out in the water.

Accordingly, the underwater mobile type inspection system of the present invention is compact and of reduced weight, and accomplishes a highly precise flaw detecting operation in all ranges to be inspected. Moreover, the inspection system of the present invention can allow an easy assembly and adjustment to reduce the number of operators needed.

When the system is applied for flaw detection of a nuclear reactor pressure vessel, a usual work period needed to carry out the operation may be shortened to $\frac{1}{4}$-1/5 of that in the prior art, and thus the system may contribute greatly to the reduction in the exposure of the operator to radiation, while simultaneously reducing the inspection period and cost.

BRIEF DESCRIPTION OF THE DRAWINGS

FIG. 11 through FIG. 15 are views respectively showing the operating mode of the mobile vehicle in alternative embodiments of the invention;

DETAILED DESCRIPTION OF THE PREFERRED EMBODIMENTS

Figure 1:
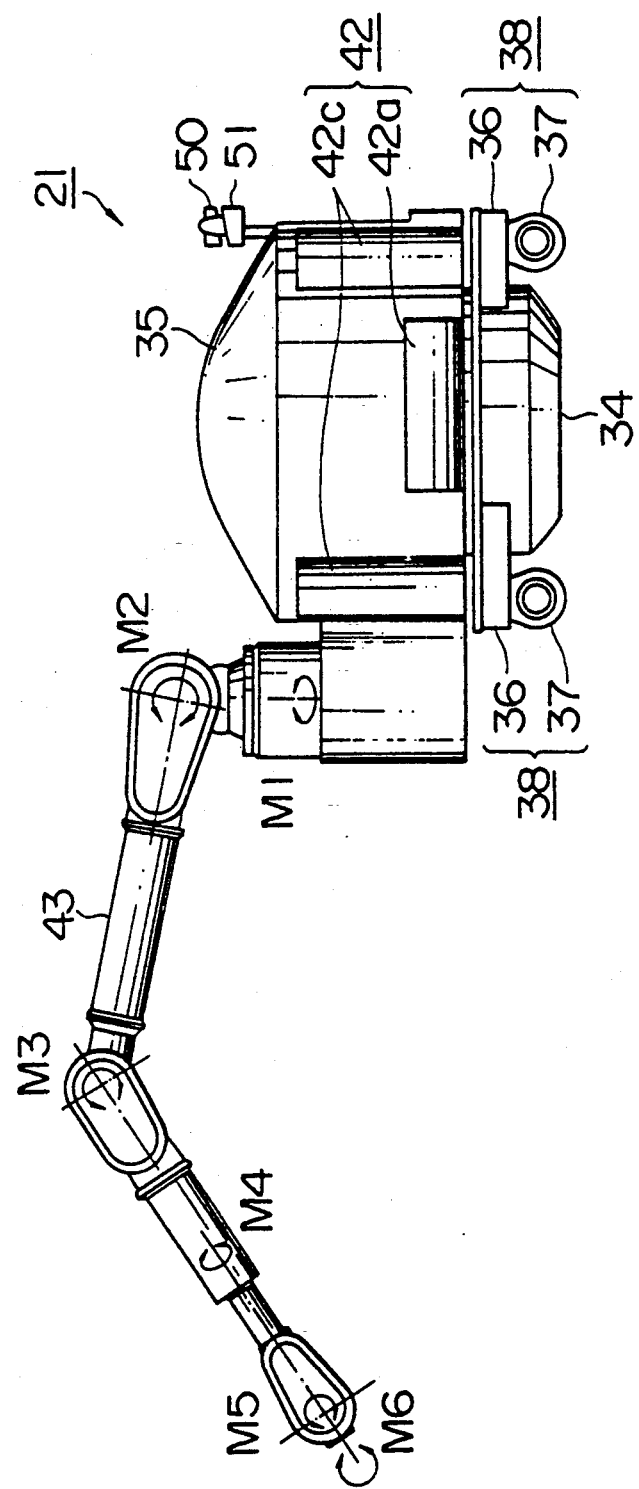
FIG. 1 is a front elevation of the mobile vehicle in the first embodiment of the underwater mobile type inspection system of the present invention.

One embodiment of the present invention will be described hereinbelow with reference to accompanying drawings wherein the same reference numerals are used to indicate the identical components throughout the drawings.

Figure 3:
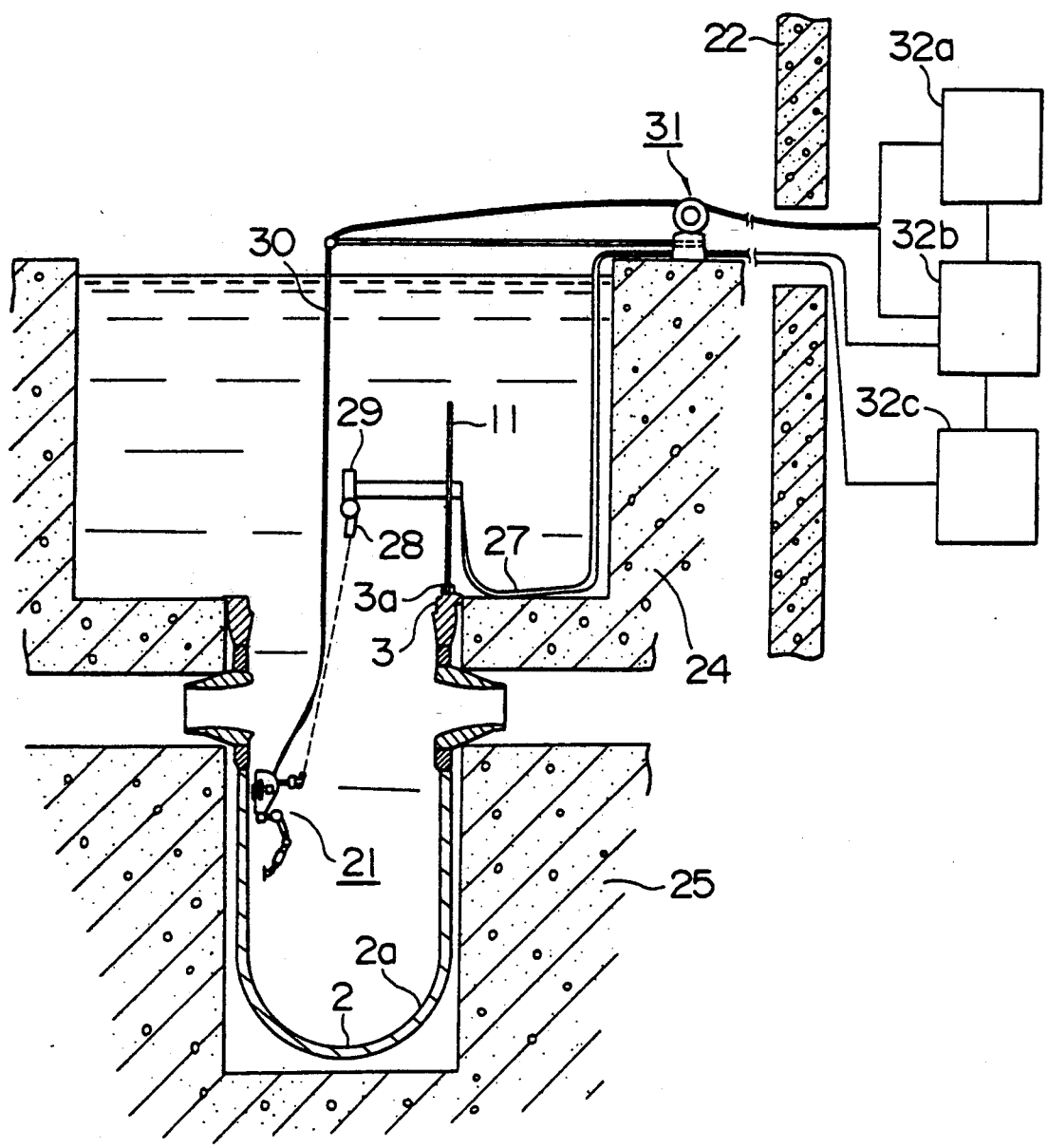
FIG. 3 is a general pictorial view showing the underwater mobile type inspection system as applied in the nuclear reactor pressure vessel to detect a defect.

FIG. 3 is a view schematically showing one embodiment of the underwater mobile type inspection system of the present invention as applied for flaw detection of welds in the nuclear reactor pressure vessel (large container) 2 in the nuclear power stations.

The underwater mobile type inspection system scans the internal wall surface 2a of the vessel so as to carry out flaw detection travelling along the internal wall surface 2a by mobile vehicle device 21.

Prior to the start-up of a flaw detection operation, a head closure (not shown) is removed beforehand from the reactor vessel 2 which is positioned below the bottom floor of the cavity pit 24 and surrounded by a concrete wall. The reactor vessel 2 and the cavity pit 24 are filled with water to shield radiation. A seal is disposed between the upper flange 3 of the reactor vessel 2 and the bottom floor of the cavity pit 24. The reactor vessel 2 and the cavity pit 24 etc. are enclosed by a concrete container which is generally called a nuclear reactor containment vessel 22, and this vessel 22 serves to completely shield radiation.

Connected to the mobile vehicle device 21 are a cable 30 which includes lines through which flaw detecting signals and control signals etc. are transmitted, and power lines.

Provided above the cavity pit 24 is a cable length adjustment and guide device 31 which serves to guide the cable 30 while adjusting the cable length to be submerged into the water, depending on the moving position of the mobile vehicle device 21. The cable 30 is connected to an ultrasonic inspection device 32a which processes flaw detecting data transmitted via the cable length adjustment and guide device 31 from the mobile vehicle device 21, and to a position controller 32b which acts to control the position of the mobile vehicle device 21. The ultrasonic inspection device 32a and the position controller 32b are arranged outside the nuclear reactor containment vessel 22 for shielding them from radiation.

A guide stud 11 extends vertically and is threadably engaged with one of a plurality of bolt holes 3a drilled through the upper flange 3. The bolt holes 3a are machined in order that the head closure (not shown) may be removably fixed in position on the upper flange 3 of the reactor vessel by means of bolts.

In the present embodiment, a distance determining device 28 (position orientation means) for orienting the position of the mobile vehicle device 21, and a two-axes position locating and driving device (position orientation means) 29 for orienting the distance determining device 28 in a direction to the mobile vehicle device 21 are mounted substantially at an intermediate position of the guide stud 11.

A cable 27 is connected at one end with the distance determining device 28 and the position locating and driving device 29, and communicates at its opposite end with the position control device 32b and a position locating device (position orientation means) 32c which are arranged outside the nuclear reactor containment vessel 22.

The position control device 32b not only controls the position of the mobile vehicle device 21, but also controls the position of the position locating and driving device 29. The position locating device 32c is electrically connected with the position control device 32b and functions to determine the absolute position of the mobile vehicle device 21 with reference to distance data transmitted from the distance determining device 28 via the position control device 32b, and location data transmitted from the position locating and driving device 29.

Then, the construction of the mobile vehicle device 21 will be described in details hereinbelow with reference to FIG. 1 and FIG. 2.

The mobile vehicle device 21 comprises mounting base 34 of a shell structure, the mounting base 34 having a turning base 35 secured thereon for slewing movement. The mounting base 34 is also provided with a running gear 38 which comprises a suitable number (four in this embodiment at each corner) of wheels 37 each of which may swing about its own axis for free rotation via a steering mechanism 36 in all directions. The mobile vehicle device 21 may travel freely along the wall surface 2a of the reactor vessel 2 in all directions. A plurality of adhesion devices 41 are provided with an adhesion pad 40 which can move vertically by means of an actuator 39 so as to secure the mobile vehicle device 21 directly on the wall surface 2a.

The turning base 35 is in turn provided with a suitable number of thrusters 42a, 42b each of which is disposed to cause the mobile vehicle device 21 to submerge and float relative to the reactor vessel 2, and with a suitable number of thrusters 42c, 42d each of which is disposed to cause the mobile vehicle device 21 to move toward and away from the wall surface of the nuclear reactor pressure vessel 2. The mobile vehicle device may travel freely in the water in three-dimensional directions being driven by a propulsion unit 42 comprising these thrusters 42a, 42b and 42c, 42d. An articulated manipulator 43 with the six degrees of freedom of motion extends from the turning base 35 in this embodiment.

A probe 44 is attached at the tip end of the manipulator, which probe 44 operates to detect flaws in the wall portion of the reactor vessel 2. Furthermore, an orientation marker 50 is secured in position on the upper part of the turning base 35 via a two-axis driving device 51 as a target of the distance determining device 28 for orienting the device.

Then, the structure of the mobile vehicle device 21 will be described hereinbelow, along with the details of each of mechanisms, with reference to accompanying drawings FIG. 4 through FIG. 9.

Figure 4:
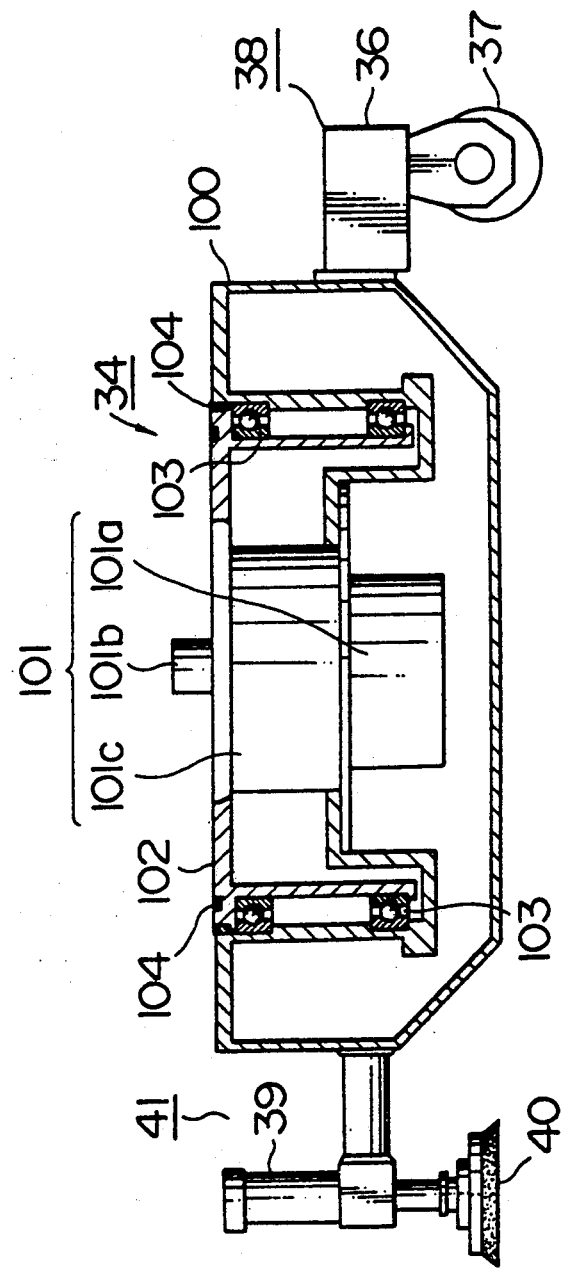
FIG. 4 through FIG. 9 are pictorial views respectively showing the components of the mobile vehicle device in the above embodiment.

FIG. 4 is pictorial view of the mounting base 34 which has a rotational driving mechanism 101 arranged at the center of a anchoring base body 100. The rotational driving mechanism 101 is located in co-axial alignment with a motor 101a as a driving source, an encoder 101b for detecting the position, and a reduction gear 101c for boosting up the drive force from the motor 101a. While the reduction gear body 101c is mounted on the anchoring base body 100, the output shaft 102 of the reduction gear is freely turnably supported on a bearing 103 which is in turn provided on the anchoring base body 100. Around the output shaft 102 of the reduction gear, a sealing material 104, such as an O-ring, are mounted to seal the interior of the mounting base 34.

A suitable number of travelling devices 38 and adhesion devices 41 are disposed on the outer periphery of the mounting base 34.

Figure 5:
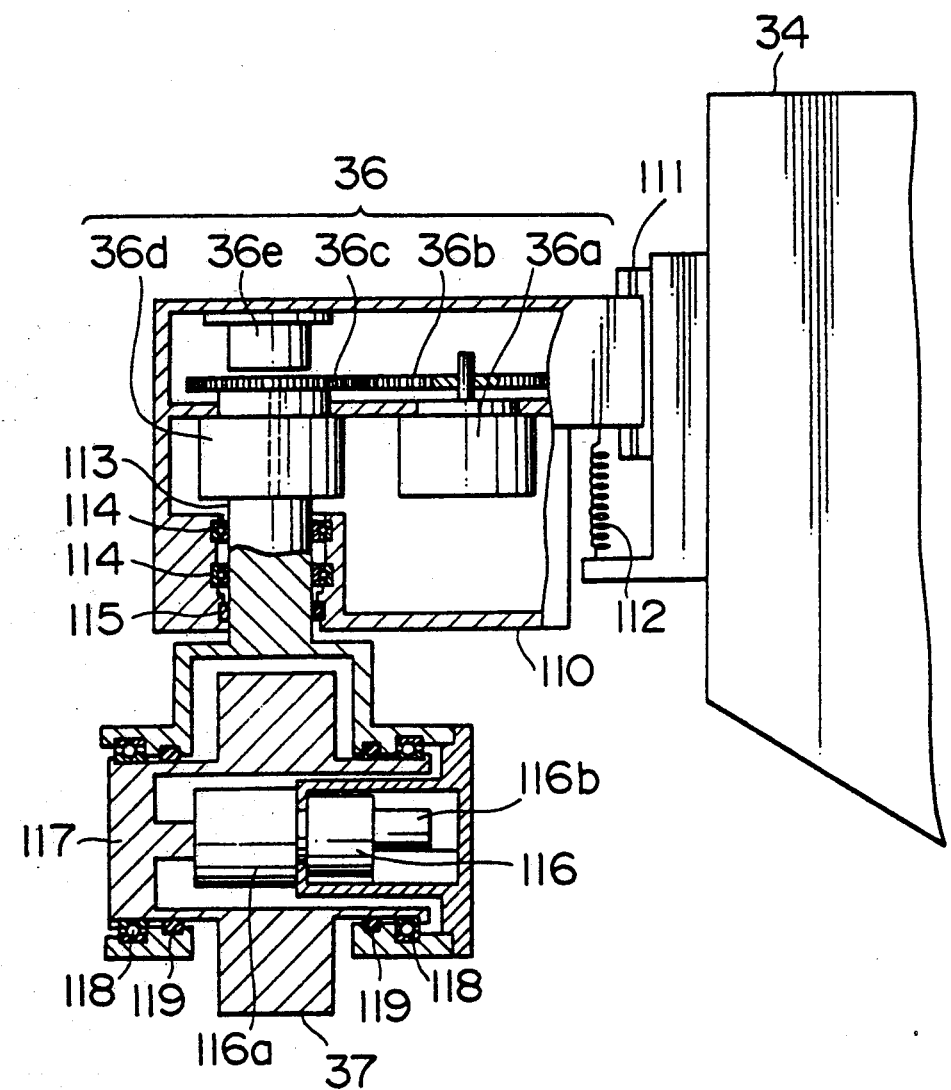

In the mobile vehicle device as shown in FIG. 5, a mobile vehicle device body 110 is mounted on the mounting base 34 via linear bearings 111 such that the body 110 may move freely downwardly and upwardly under the resiliency of a spring 112 arranged at opposite sides of the linear bearings 111. A steering mechanism 36 for pivotably driving the wheel 37 is arranged inside the mobile vehicle device body 110.

In the steering mechanism 36 motor 36a serves as the source of a driving force which is fixed in position on the mobile vehicle device body 110. A gear 36b is connected to the output shaft of the motor 36a, and the reduction gears 36d engage with the gear 36b. The output shaft 113 of the reduction gears 36d (because this gear is an internal rotary reduction gear of a known structure, its detail description will be omitted herein) is turnably supported by means of bearings 114 which are disposed on the mobile vehicle device body 110. The output shaft 113 of the reduction gears 36d is provided with a sealing material 115, such as an O-ring, for sealing the interior of the mobile vehicle device body 110, and with a wheel drive mechanism 116 for driving the wheels. The output shaft 113 of the reduction gears 36d is provided with a potentiometer 36e which operates to detect the position.

The wheel drive mechanism 116 is of the same construction as the driving mechanism 101 of the turning base, wherein the output shaft 117 of the reduction gears 116a is coupled to the wheels 37, and travelling movement is carried out by turning the wheels 37. In a similar manner as described above, the output shaft 117 of the reduction gears 116a is provided with a sealing member 119 such as the O-ring for sealing off the interior of the wheel drive mechanism 116b. An encoder 116 which can measure the rotation of the wheels is provided on the output shaft of the reduction gears 116a.

Figure 6:
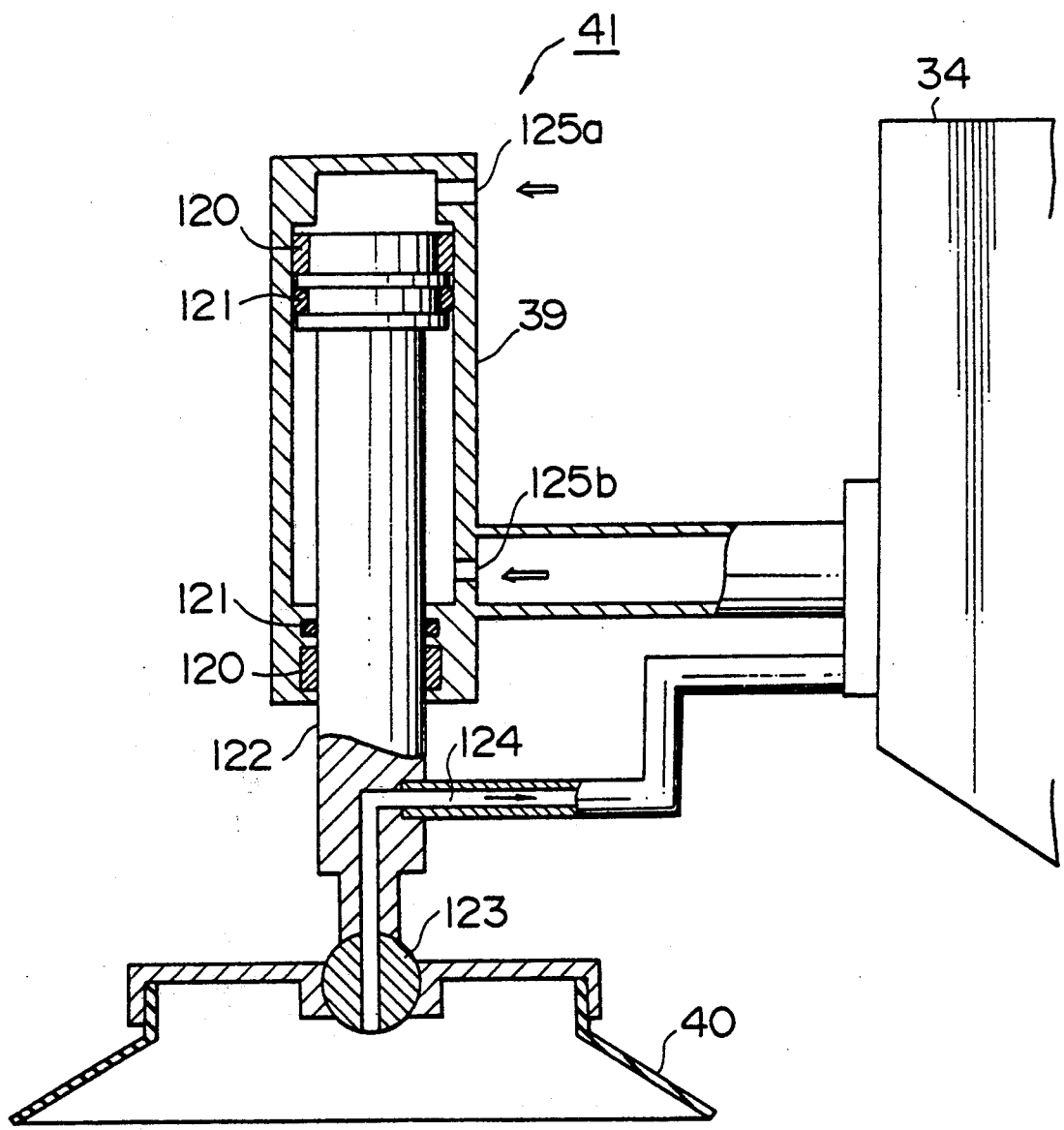

In the adhesion device 41, as shown in FIG. 6, the actuator cylinder tube 39 is mounted on the mounting base 34, and a piston rod 122 is provided in the interior of the cylinder tube 39 with bearings 120 and sealing member 121.

An adhesion pad 40 is attached at the tip end of the piston rod 122 by means of spherical bearings 123, and a vacuum passage 124 in the tip end of the piston rod 122 is open at the internal surface of the adhesion pad 40. By vacuum exhausting through this vacuum passage 124, a vacuum is created in the adhesion pad 40, and thus the adhesion pad 40 may be pressed against the wall surface 2a of the reactor vessel 2. Pneumatic inlet ports 125a and 125b are defined in an area intermediate between the upper end and the central portion of the cylinder tube, and the piston rod 122 may be moved in a vertical direction in the Figure, by introducing a pneumatic pressure to either the pneumatic inlet port 125a or 125b.

Figure 7:
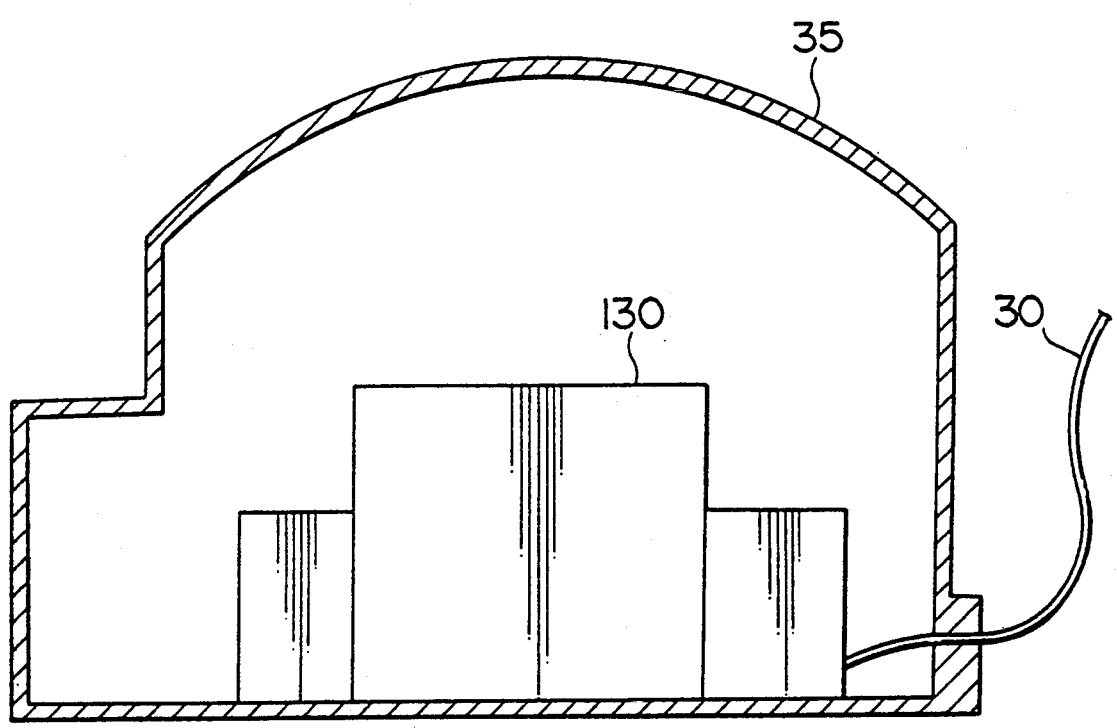

FIG. 7 is a pictorial view of the slewing or turning base 35. The slewing base 35 become rotatable by fixing it on a reduction output shaft 102 of a pivot driving mechanism 101 attached on the anchoring base body 100. Arranged inside the slewing base 35 are an amplifier for driving a motor of each driving mechanism and an electric box 130 which contains A/D, D/A, E/O, O/E converters etc. therein. These A/D, D/A, E/O, O/E converters are adapted to convert commands from the position control devices 32b and data for transmission to the position control devices 32b. A fine and light-weight cable 30 which extends outside the slewing base is connected with the electric box 130.

A six-axis articulated manipulator 43 is fitted in position on the outer periphery of the pivot base 35 (the manipulator being of a known type, its description is omitted herein). An orientation marker 50 is secured in position at the rearward portion of the slewing base 35.

Figure 8:
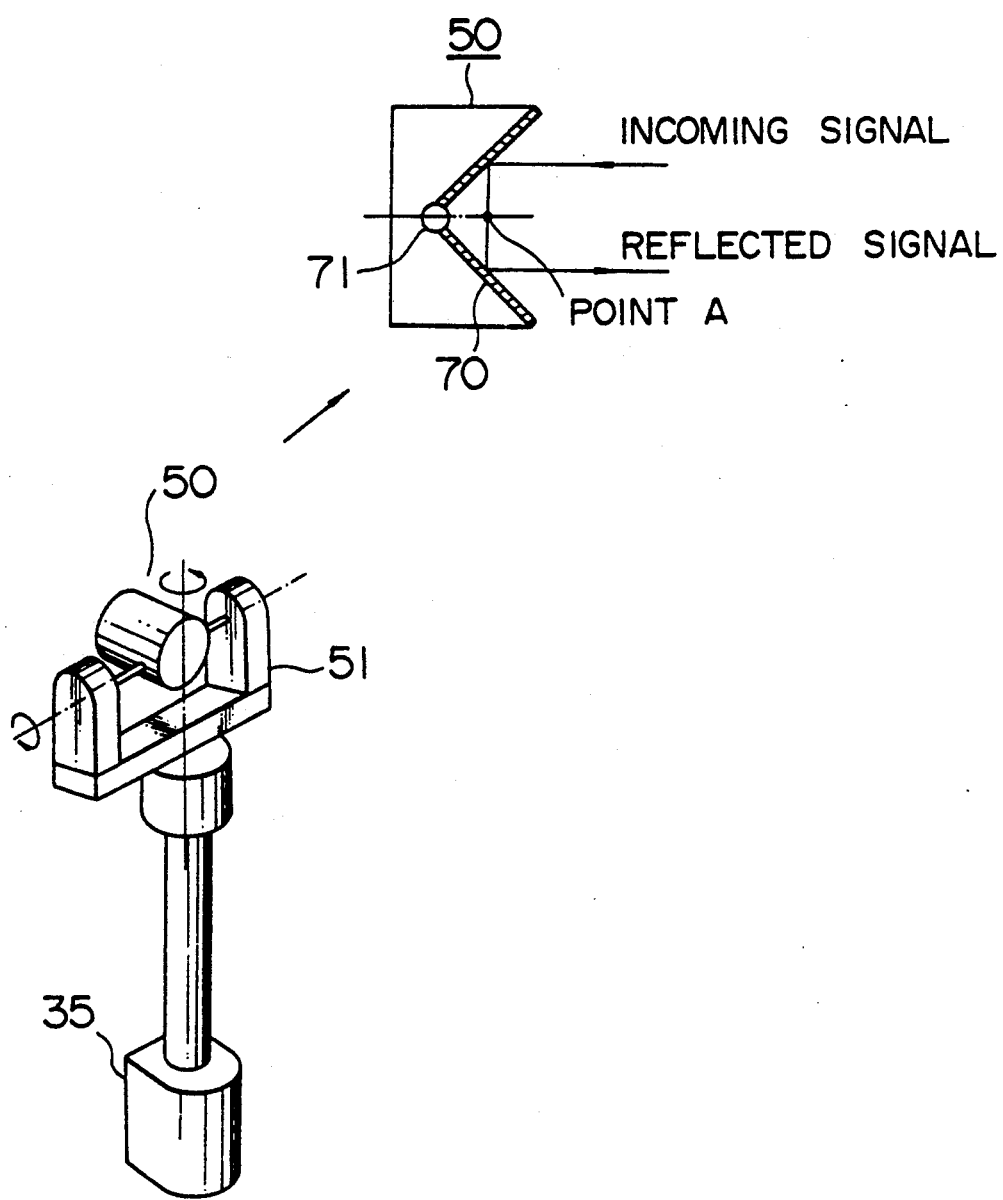

Referring to FIG. 8, the orientation marker 50 is composed of a corner cube 70 and a global light source 71 which is disposed at the center of the corner cube 70. The orientation marker may turn around a point A where an incidence light into the corner cube is reflected off and where the center line of the corner cube intersects with the reflected light. The orientation marker 50 is attached to the slewing base 35 via the driving device 51 which moves up and down.

Figure 9:
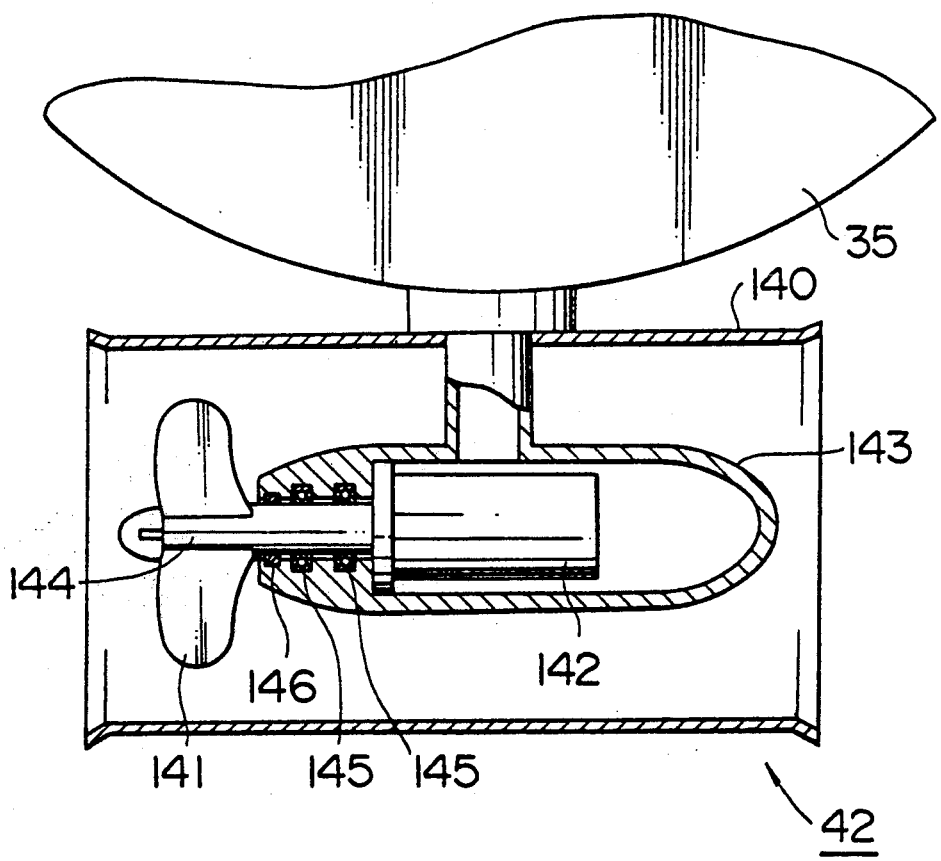

FIG. 9 is a pictorial view of the propulsion unit 42. Disposed inside the thruster cover 140 attached on the slewing base 35 is a motor 142 via a streamline-shaped motor cover 143, which motor 142 operates to drive the screw 141. Freely rotatably mounted at the tip end of the output shaft 144 of the motor is the screw 141 with bearings 145 and the seals 146 which are secured in the motor cover 143.

By turning the screw 141 in a normal or reverse direction, the vehicle device may be submerged and floated by means of the thrusters 42a, 42b, which are arranged in parallel with the pivot base 35, whereas it may move toward and away from the wall surface 2a by means of the thrusters 42c, 42d which are arranged vertically relative to the slewing base 35.

Figure 10:
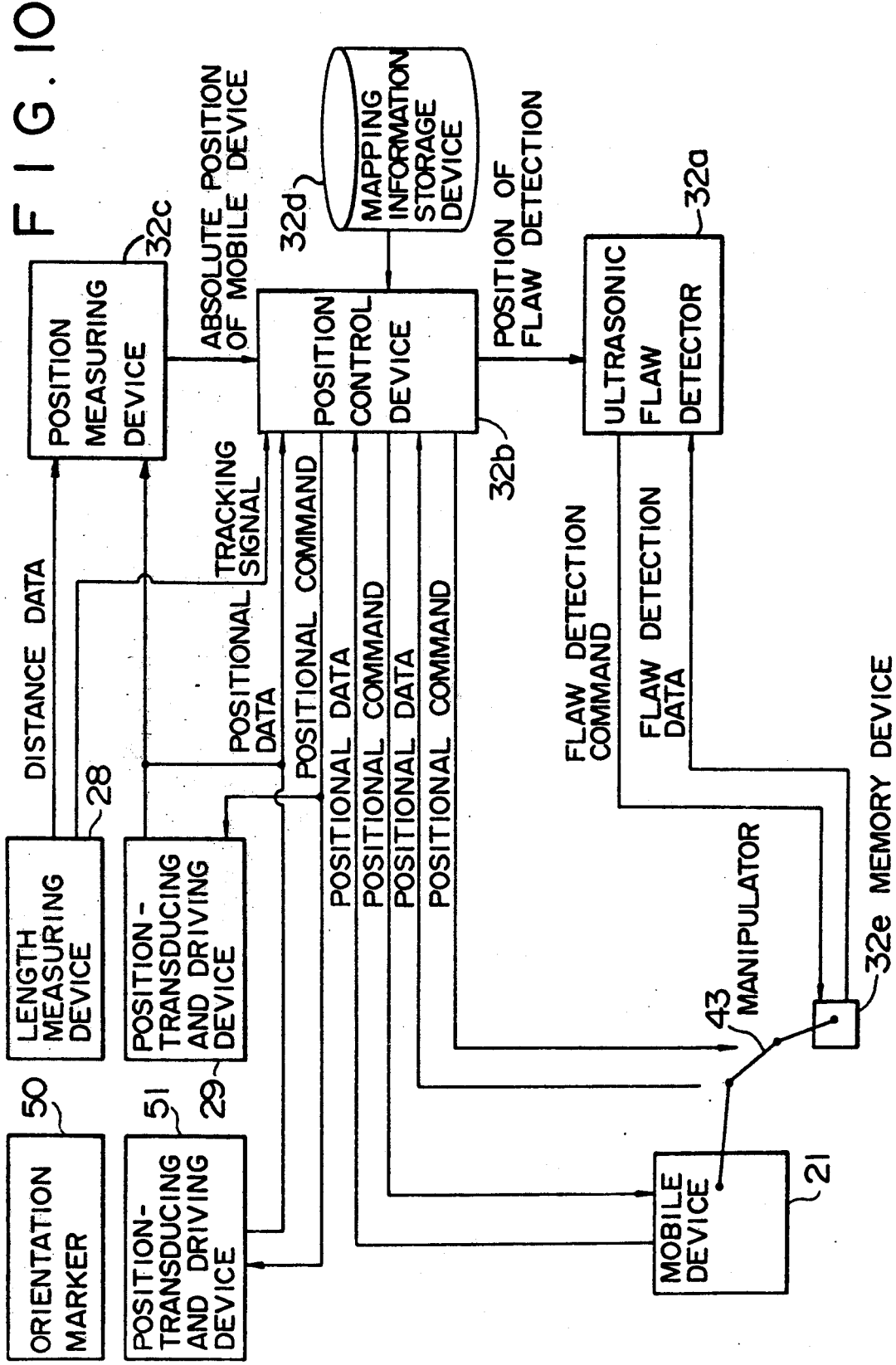
FIG. 10 is a block diagram showing the flow of signals in the underwater mobile type inspection system shown in FIG. 3.

FIG. 10 is a block diagram which shows the flow of signals in the underwater mobile type inspection device in the above embodiment. Stored beforehand in the map memory device 32d shown in FIG. 10 is so-called mapping information, such as sequence of the flaw detection operation by the mobile vehicle 21 along the wall surface, a stop position of the mobile vehicle 21 made immovable on the wall surface and an operation sequence of the manipulator 43. These data are used in the sequence given below to undertake an ultrasonic inspection operation.

Figure 11:
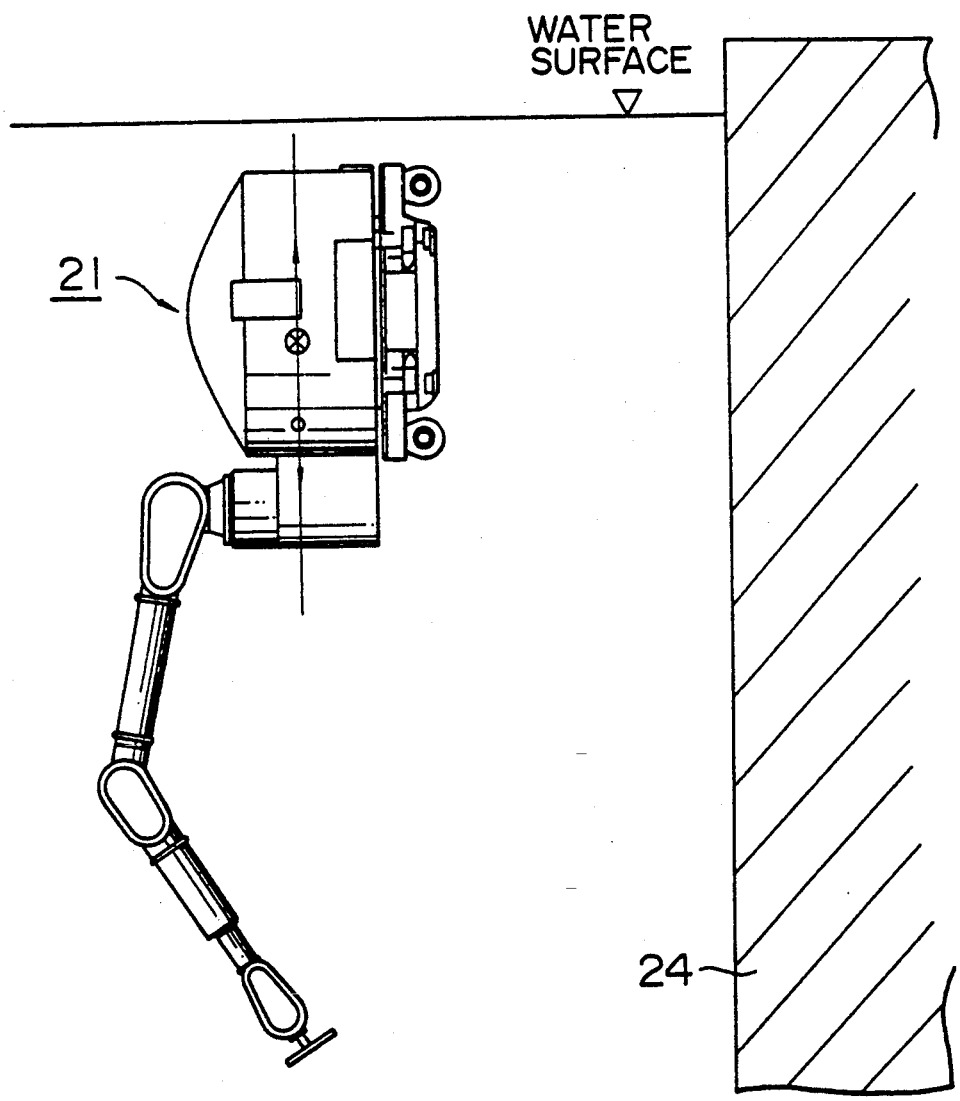

(1) The mobile vehicle device 21 is lifted above the water surface and kept afloat on the surface (the weight of the mobile vehicle 21 is 0 kgf in the water. Because of a relationship established between the center of gravity of the mobile vehicle device body and its center of buoyancy as shown in FIG. 11, the mobile vehicle device may stand up vertically and maintain its stable position in the water).

(2) The vehicle may be submerged in the water by rotating the thrusters 42a and 42b.

(3) The vehicle device may be moved toward the wall surface 2a by rotating the thrusters 42c and 42d. The mobile vehicle device may be moved in a right or a lift direction by adjusting the rotation of the screws 141 for these thrusters 42c and 42d. The mobile vehicle device may turn at a fixed position by rotating the screws of the thrusters 42c and 42d on the opposite sides of the of the vehicle in different directions. In this way, the vehicle device 21 may be guided to a position on a wall surface as desired (see FIG. 12).

(4) After the mobile vehicle device 21 has come into contact with the wall surface 2a, the absolute position of the mobile vehicle device 21 relative to the reactor vessel 2 is determined by means of a non-contact type distance determining device 28.

Figure 13:
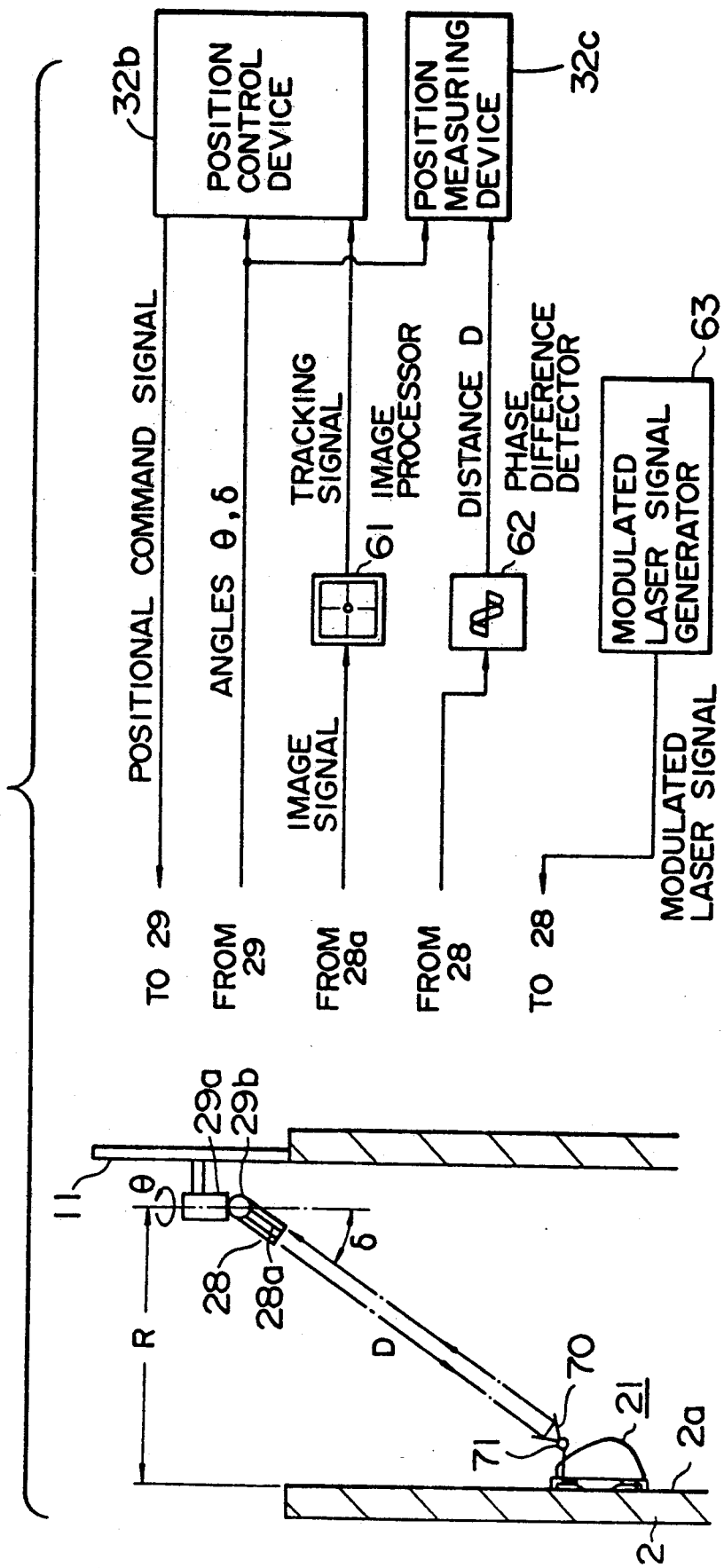
Figure 14:
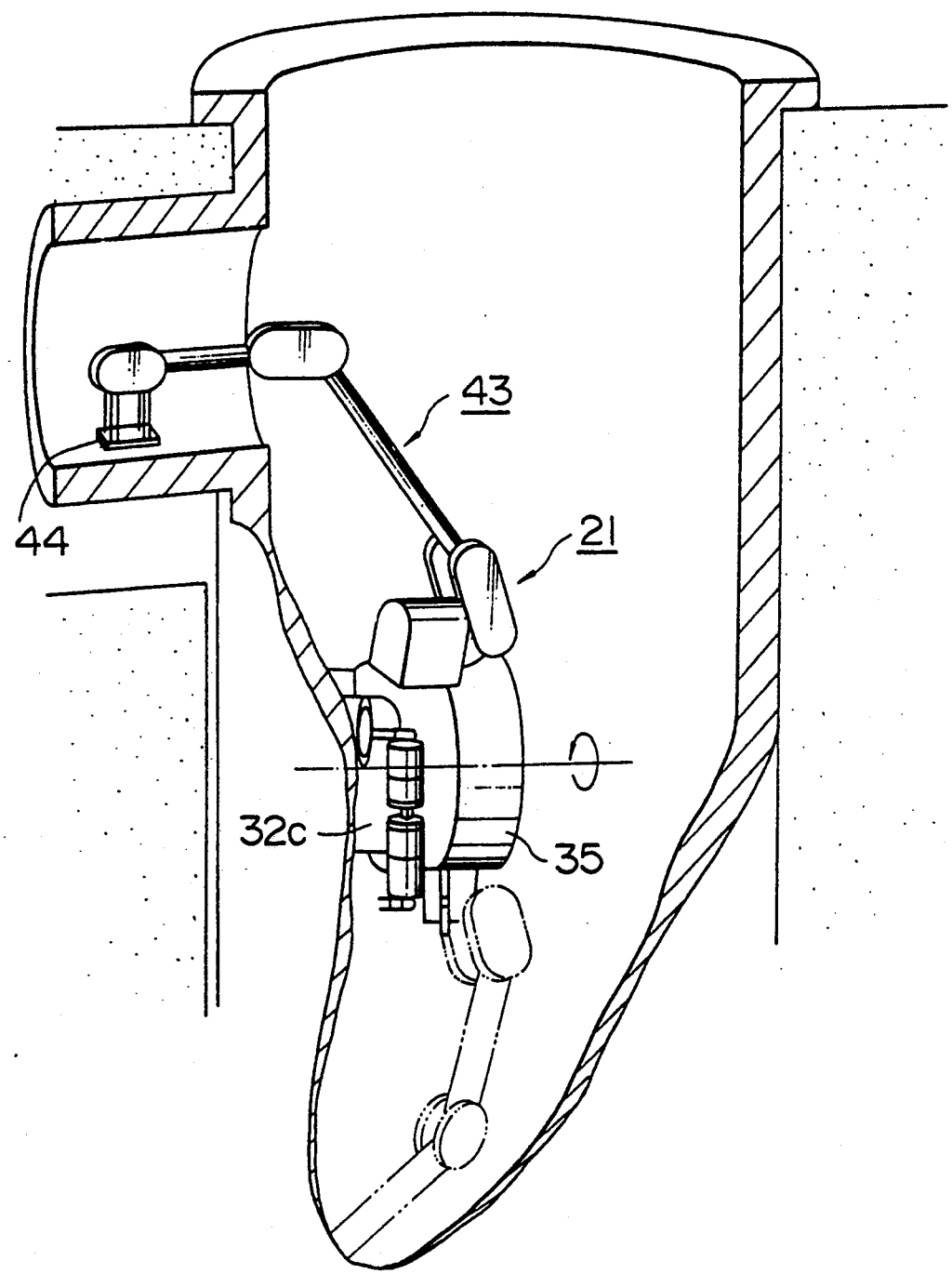

In FIG. 13, the distance determining device 28 is coupled with an image processing device 61 (not shown in FIG. 3) which operates to detect the position of the global light source 71 of the mobile vehicle device 21 as observed by the visual sensor 28a of the distance determining device 28.

The image processing device 61 has been preset with a reference position, and the device 61 inputs into a position control device 33a any deviation of the measurement from this reference position as a tracking signal. The position control device 32b operates in response to this tracking signal to input a position command signal to a position locating and driving device 29 which consists of a positioning mechanism 29a for a rotation angle $\theta$ and a positioning mechanism 29b for a pivot angle 6, the command signal indicating the target position of the device 29. The positioning and driving device 29 of the distance determining device 28 is thus controlled to point toward the orientation marker 50 of the mobile vehicle device 21, and the driving device 51 of the orientation marker 50 is thus simultaneously controlled to point toward the distance determining device 28.

The rotation direction $\theta$ and the pivot direction $\delta$ of the position locating and driving device 29 are also input to the position locating device 32c.

On the other hand, a distance between the position locating and driving device 29 and the mobile vehicle device 21 is measured by means of the distance determining device 28. In this embodiment, the distance determining device 28 uses an argon laser beam as a non-contact medium for measuring a distance. However, a sonic wave and other optical means may alternatively be used. The laser beam signal which is transmitted from the modulated laser signal generator 63 is guided, via the distance determining device 28, into the corner cube prism 70 for laser reflection in the orientation marker 50 which is secured in position on the mobile vehicle device 21, and then reflected back off the prism 70. The transmitted signal and the reflected signal are input into a phase detector 62 wherein a difference in the phase between these two signals is measured, and the distance D between the distance determining device 28 and the orientation marker 50 is calculated. The data which have been collected on the distance are likewise input to the position locating device 32c.

In the position locating device 32c, the orientation of the absolute position for the mobile vehicle device 21 are calculated in accordance with a formula given below, given a horizontal distance R between the rotation axis of the position locating and driving device 29 and the wall surface 2a of the reactor vessel 2.

Horizontal Direction: Angle $\theta$ is used as it is (which represents the angular position of the driving device 29)

Depth-wise Direction: Depth $L = D \cdot \sin(\cos^{-1} R/D)$

The absolute position of the mobile vehicle device may be known from the above calculation.

Furthermore, a position of the mobile vehicle device 21 can be obtained without dead angle, since the distance determining device 28 is attached at an upper portion in a scanning range along which the mobile vehicle device 21 may move.

(5) A flaw detecting position is retrieved from the map information storage device 32d and then fed to the position control device 32b wherein a current position of the mobile vehicle device 21 and its deviation from a reference position are utilized to compute a target position command. The driving instruction is given to the running gear 38 of the mobile vehicle device 21 to move it to a target position.

In the meantime, the mobile vehicle device may run on the surface by operating the thrusters 42c and 42d to point toward the direction of approach, and urging the mobile vehicle device 21 toward the wall surface 2a.

(6) After the mobile vehicle device 21 has reached a target position, the device stops travelling to actuate the actuation 39 of the adhesion device 41 for urging the adhesion pad 40 against the wall surface 2a and creating a vacuum in the adhesion pad. The mobile vehicle device 21 is then secured on the wall surface 2a.

(7) The mobile vehicle device is again measured for its absolute position.

Then, information for the operation of the manipulator 43 is retrieved from the map information memory device 32d and sent to the position control device 32b, and this data is utilized to actuate a driving means (not shown) which is contained in the manipulator 43 for controlling the position of the probe 44 provided at the tip end of the manipulator 43. When the probe 44 comes to a position where a flaw detection operation should be made, the ultrasonic inspection device 32a receives a signal indicating a flaw detecting position from the position control device 32b and sends the probe 44 an instruction for initiating a flaw detection operation. In this way, data concerning the results of flaw detection operation may be collected in a real time mode. Since the data about the flaw detected position is input to the ultrasonic inspection device from the position control device 32b, and thus a defective location may be identified easily if present.

At this moment, since the mobile vehicle device 21 is fixed in position relative to the wall surface 2a, and the flaw detection is done by means of the manipulator 43, the device may traverse at a fixed speed utilizing urging force imposed on the probe 44 and an improved precision in the trajectory defined by the probe 44. After the flaw detection operation is complete, the piston rod 122 is actuated to move the adhesion pad 40 away from the wall surface 2a, and the mobile vehicle device 21 is thus released from its fixed position.

(8) By repeating the above sequences (5)-(7) a flaw detection operation may be undertaken covering a range as desired.

Figure 2:
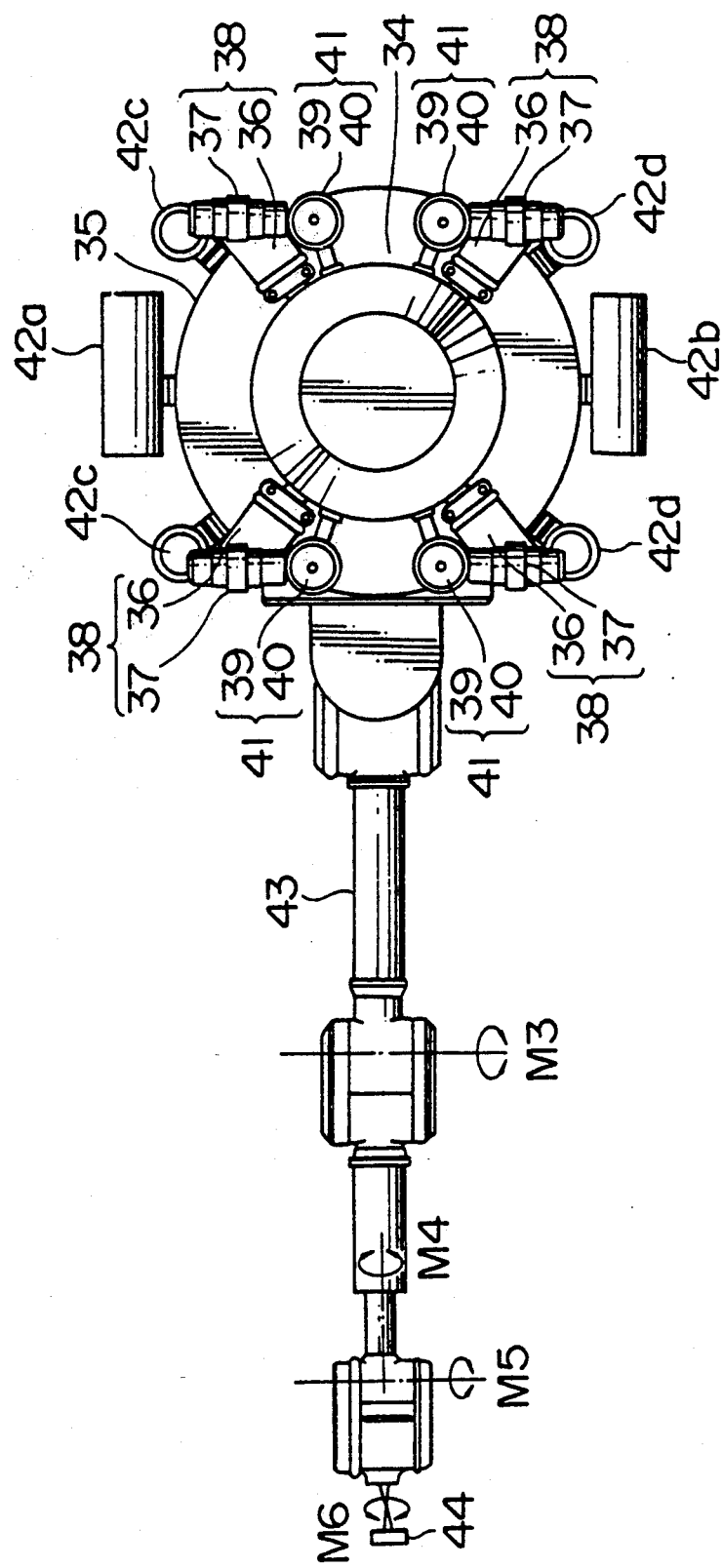
FIG. 2 is a bottom plan view in the same embodiment in FIG. 1.

When a flaw detecting position is located at the upper portion of the mobile vehicle device 21 (which may be located at, for example, the interior surface of the nozzle etc. as shown in FIG. 1), the position of the manipulator 43 may be varied to carry out a flaw detection operation, by actuating the slewing base 35 to turn.

Figure 15:
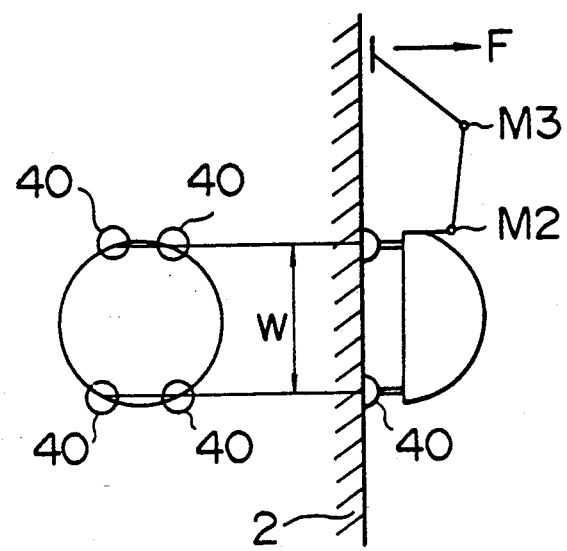

By arranging the adsorption pads 40 as shown in FIG. 15, the reaction from the manipulator is received by the adhesion pads 40 with an extended distance W spaced therebetween. Consequently, the effect of the force F can be reduced, and the anchoring carriage can be placed stably in a fixed location.

Figure 17:
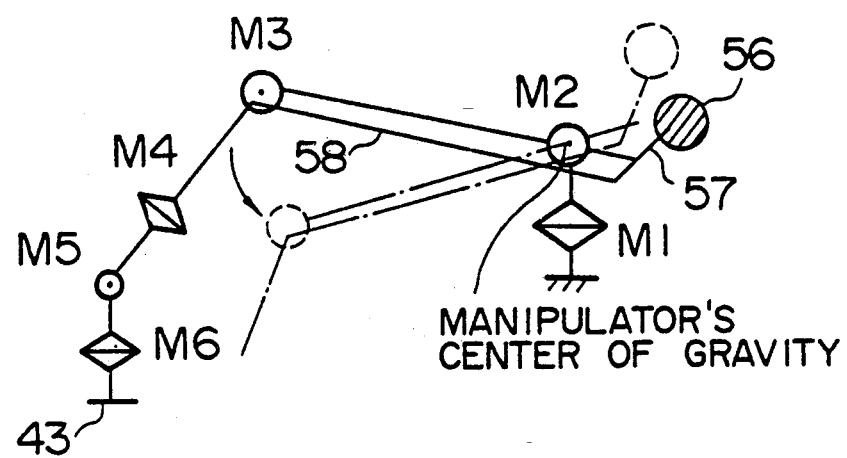
FIG. 16 and FIG. 17 are pictorial views generally showing the second embodiment of the system of the present invention.

A second embodiment of the present invention now will be described with reference to FIG. 16 and FIG. 17.

The similar parts as those in the first embodiment are indicated with the same reference numerals and their description is omitted.

The second embodiment is an alternative to the first embodiment obtained by modifying the latter so that a counterweight 56 is provided to the manipulator 43 in the first embodiment via a linkage.

Figure 16:
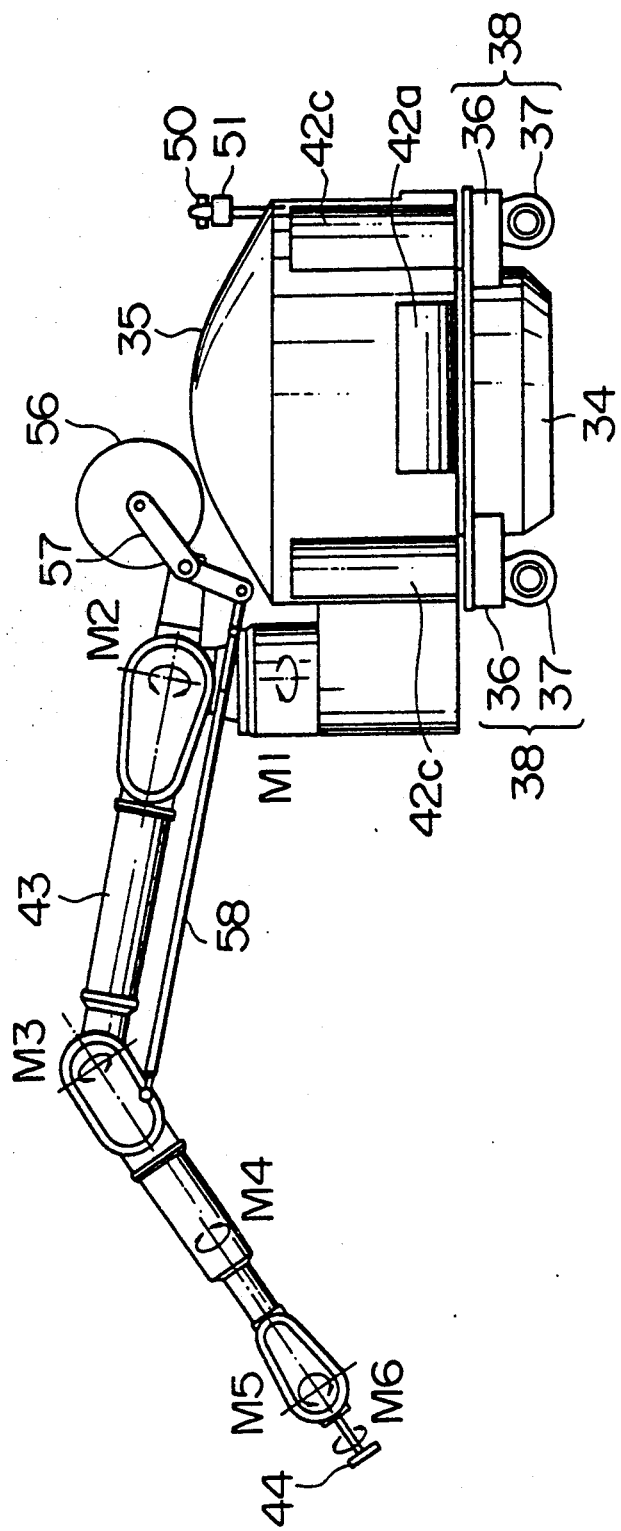
Figure 18:
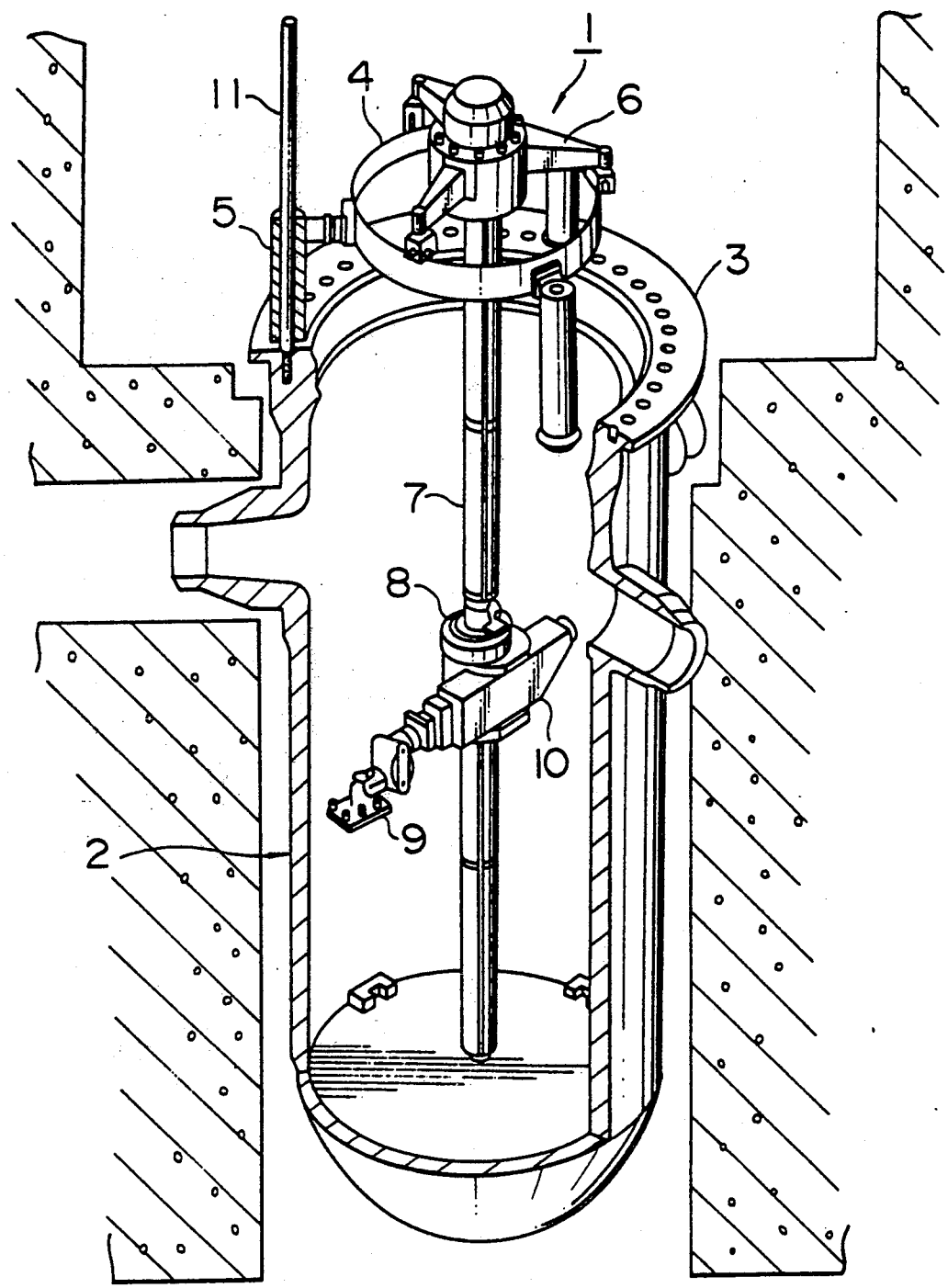
FIG. 18 is a cross-sectional view showing a conventional ultrasonic defect finding device.
Figure 19:
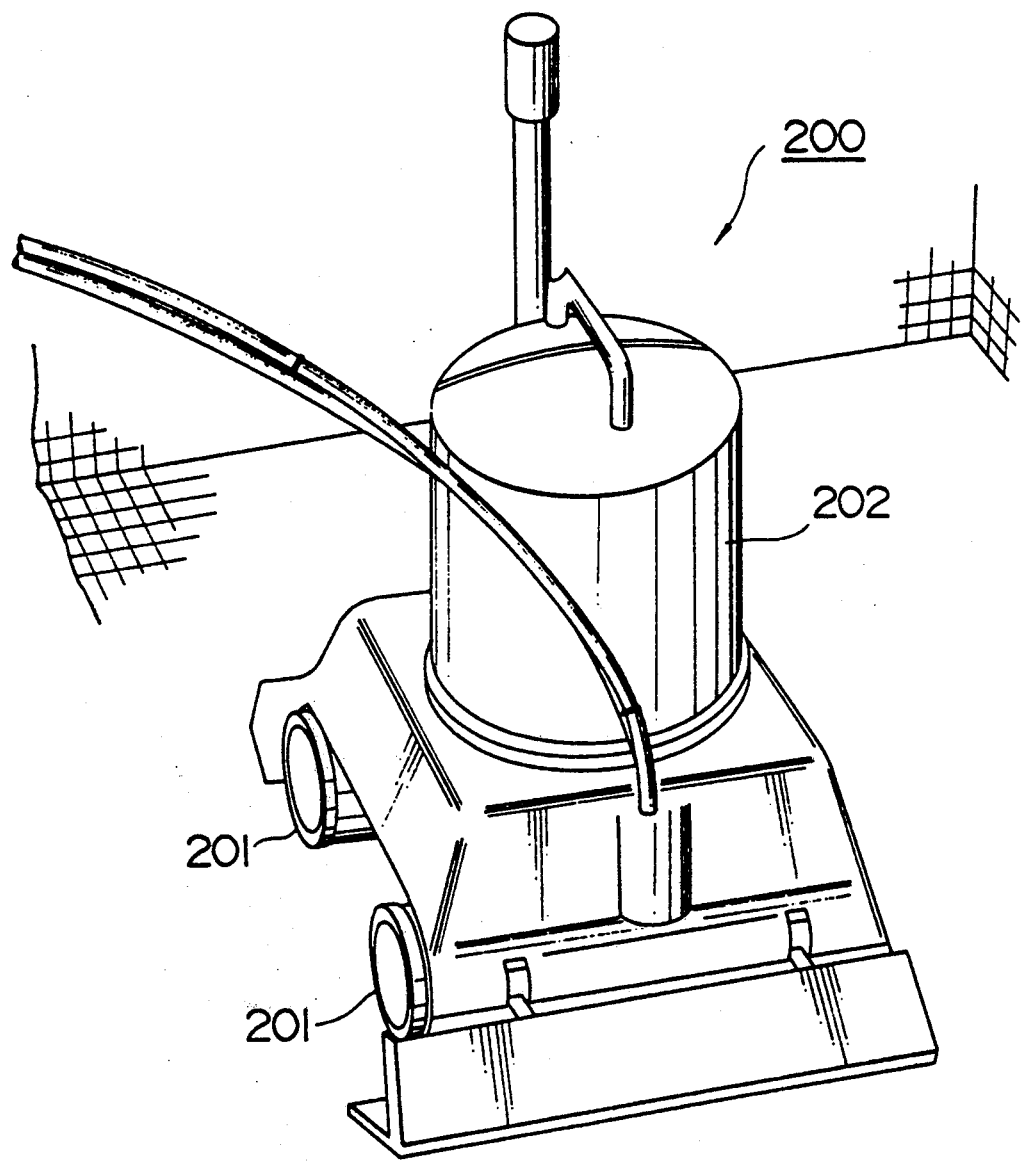
FIG. 19 and FIG. 20 are views respectively showing the general configurations of the prior underwater mobile vehicles.
Figure 20:
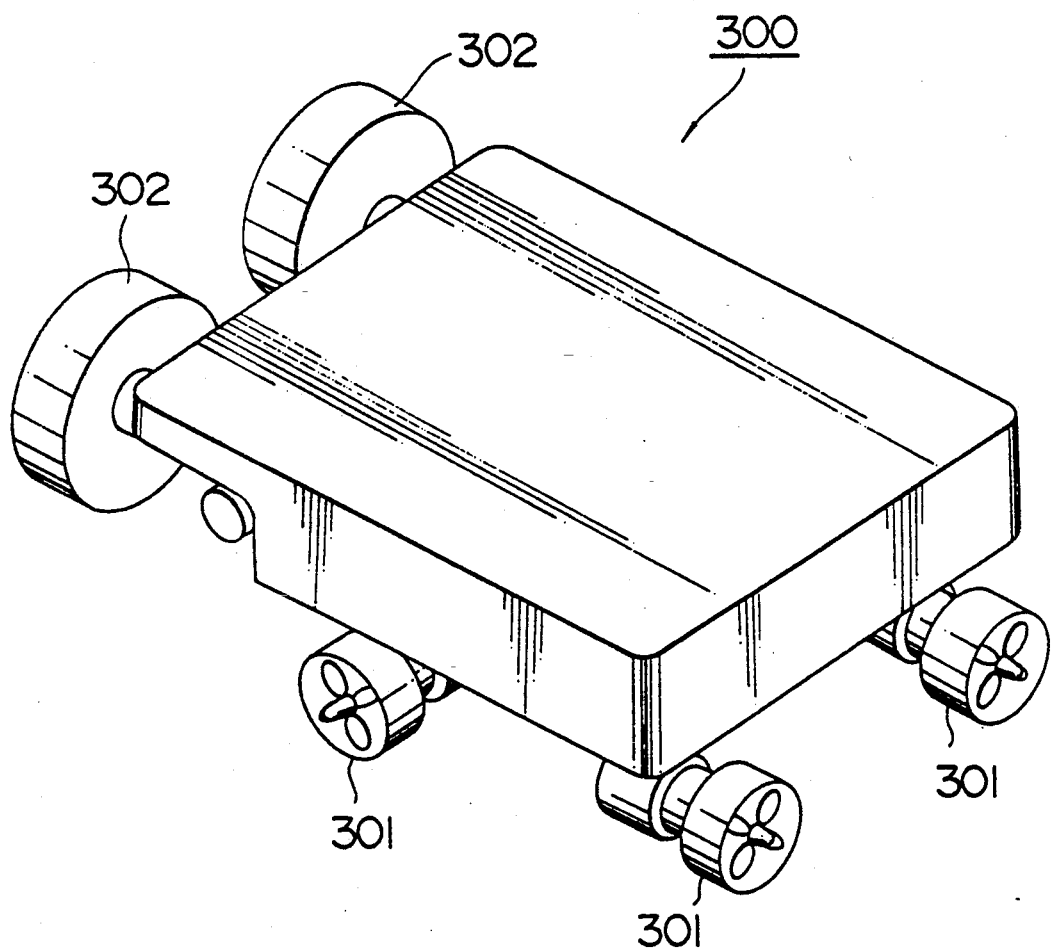

As shown in FIG. 16, there is provided a lever 57 which is freely rotatably attached to a M2 driving section body which is equivalent to a shoulder portion. A rod 58 is freely rotatably attached to a M3 driving section which is equivalent to an elbow portion at one end of the rod 58. The counterweight 56 is fixed in position at an opposite end of the lever 57.

By adding the counterweight 56, it becomes possible to locate the manipulator 43 so that its center of gravity is on the M2 driving axis, and thus the manipulator 43 does not alter the position of its center of gravity even when the position of the manipulator 43 is changed. As a result, no variation in the load to be imposed upon the adhesion pads 40 occurs, and a further improved stability is ensured in securing the device to the wall surface, and thereby ensuring a highly precise defect finding operation.

Meanwhile, the present invention has been described for its application for finding a defect on a nuclear reactor pressure vessel by means of ultrasonic means, but as obvious to those skilled in the art, the inspection system of the present invention may also be applicable to a defect finding operation for various pipings, and other structures in various plants such as nuclear power stations. The present invention may also be applicable to an inspection system which needs positioning in a wide area, such as ECT devices and inspection devices, by attaching an ECT (eddy current defect finding test) tool or an TTV camera (industrial television camera) on the tip end of the manipulator or the mobile vehicle device.

Furthermore, the mobile type inspection system of the present invention may also be used in various operations, such as the cleaning of debris off the wall surface area and the recovery of floating materials from the water, by attaching a single-purpose tool to the tip end of the manipulator.

As described above, the underwater mobile type inspection system of the present invention comprises a mobile vehicle device adapted to move to any position within a large vessel while travelling along the wall surface, and the system may be constituted in a compact configuration with a reduced weight by fitting an adsorption device and a manipulator to the mobile vehicle body. The inspection system may also be constituted for allowing its easy assembly, fitting and adjustment by eliminating the need of ancillary equipments which would otherwise be required in position on a large-sized vessel body in the traditional device. Furthermore, the inspection system of the present invention can be controlled to shift in a very short period by means of a propulsion device in a three-dimensional space even when an intended site of operation is substantially spaced apart. Because the absolute position of the mobile vehicle device can be located, the system allows a defect finding operation with an increased precision. Consequently, the system of the present invention which is compact and light in weight can find an application in a wide range of defect finding operations with an increased precision, and the assembly and the subsequent adjustment of the inspection system can be made easier to reduce the number of workers needed. Moreover, a work period which is needed to undertake the defect finding operation in the nuclear reactor pressure vessel can be shortened to $\frac{1}{4}$-1/5 of that usually taken in a traditional inspection procedure. This greatly contributes to the reduction of the exposure of operators to radiation, while simultaneously cutting a work period and saving cost.

We claim:

1. An underwater mobile type inspection system comprising an articulated manipulator having a probe attached at its tip end thereof, a turning base which supports the proximal end of said manipulator for free rotation, said turning base having propulsion means for moving said turning base underwater without any external mechanical support, a mounting base attached to the bottom of said turning base via a pivot driving mechanism, adhesion means for temporarily securing said mounting base to a surface being inspected, and travelling means mounted on an outer periphery of said mounting base to facilitate movement of said mounting base and the attached turning base along the surface being inspected.

2. The underwater mobile type inspection system as claimed in claim 1, further comprising an orientation marker, and driving means for attaching said orientation marker to said turning base so that a direction of said orientation marker may be made variable.

3. The underwater mobile type inspection system as claimed in claim 2, wherein said pivot driving mechanism mounted at the bottom of said turning base and said travelling means mounted on an outer periphery of said mounting base are provided with a detector for sensing the rotation angle and rotation speed of said inspection system.

4. The underwater mobile type inspection system as claimed in claim 2 wherein said inspection system may be 0 kgf in weight in the water, and may be movable in any three-dimensional direction in water.

5. The underwater mobile type inspection system as claimed in claim 2, wherein the elbow axis and the shoulder axis of said articulated manipulator are connected to each other by a link mechanism comprising a rod and a lever, said inspection system further comprising a counterweight connected to one end of said link mechanism.

6. The underwater mobile type inspection system as claimed in claim 2, wherein said orientation marker comprises a corner cube and a global light source, said inspection system further comprising laser distance determining means provided at a fixed position for determining the absolute position of said system.

7. The underwater mobile type inspection system as claimed in claim 6, wherein said pivot driving mechanism mounted at the bottom of said turning base and said travelling means mounted on an outer periphery of said mounting base are provided with a detector for sensing the rotation angle and rotation speed of said inspection system.

8. The underwater mobile type inspection system as claimed in claim 6 wherein said inspection system may be 0 kgf in weight in the water, and may be movable in any three-dimensional direction in water.

9. The underwater mobile type inspection system as claimed in claim 6, wherein the elbow axis and the shoulder axis of said articulated manipulator are connected to each other by a link mechanism comprising a rod and a lever, said inspection system further comprising a counterweight connected to one end of said link mechanism.

10. The underwater mobile type inspection system as claimed in claim 1, wherein said pivot driving mechanism mounted at the bottom of said turning base and said travelling means mounted on an outer periphery of said mounting base are provided with a detector for sensing the rotation angle and rotation speed of said inspection system.

11. The underwater mobile type inspection system as claimed in claim 10 wherein said inspection system may be 0 kgf in weight in the water, and may be movable in any three-dimensional direction in water.

12. The underwater mobile type inspection system as claimed in claim 10, wherein the elbow axis and the shoulder axis of said articulated manipulator are connected to each other by a link mechanism comprising a rod and a lever, said inspection system further comprising a counterweight connected to one end of said link mechanism.

13. The underwater mobile type in spection system as claimed in claim 1, wherein said inspection system may be 0 kgf in weight in the water, and may be movable in any three-dimensional direction in water.

14. The underwater mobile type inspection system as claimed in claim 13, wherein the elbow axis and the shoulder axis of said articulated manipulator are connected to each other by a link mechanism comprising a rod and a lever, said inspection system further comprising a counterweight connected to one end of said link mechanism.

15. The underwater mobile type inspection system as claimed in claim 1, wherein the elbow axis and the shoulder axis of said articulated manipulator are connected to each other by a link mechanism comprising a rod and a lever, said inspection system further comprising a counterweight connected to one end of said link mechanism.

16. An underwater mobile type inspection system comprising:
   an articulated manipulator having a probe attached at its tip end thereof;
   the elbow axis and the shoulder axis of said articulated manipulator being connected to each other by a link mechanism comprising a rod and a lever;
   a counterweight connected to one end of said link mechanism;
   a turning base which supports the proximal end of said manipulator for free rotation;
   propulsion means for moving said turning base underwater without any external mechanical support;
   a mounting base attached to the bottom of said turning base via a pivot driving mechanism;
   adhesion means for temporarily securing said mounting base to a surface being inspected;
   travelling means mounted on an outer periphery of said mounting base to facilitate movement of said mounting base and the attached turning base along the surface being inspected;
   said pivot driving mechanism and said travelling means being provided with a detector for sensing the rotation angle and rotation speed of said inspection system;
   an orientation marker comprising a corner cube and a global light source;
   driving means for attaching said orientation marker to said turning base so that a direction of said orientation marker may be made variable; and
   laser distance determining means provided at a fixed position for determining the absolute position of said inspection system.

17. The underwater mobile type inspection system as claimed in claim 16, wherein said inspection system may be 0 kgf in weight in the water, and may be moveable in any three-dimensional direction in water.

* * * * *